(12) United States Patent
Kawamura et al.

(10) Patent No.: US 8,002,754 B2
(45) Date of Patent: Aug. 23, 2011

(54) PLUNGER ROD AND SYRINGE

(75) Inventors: Hideaki Kawamura, Tokyo (JP);
Hiroshi Togashi, Tokyo (JP)

(73) Assignee: Daikyo Seiko, Ltd., Tokyo (JP)

( * ) Notice: Subject to any disclaimer, the term of this patent is extended or adjusted under 35 U.S.C. 154(b) by 139 days.

(21) Appl. No.: 12/265,271

(22) Filed: Nov. 5, 2008

(65) Prior Publication Data
US 2009/0131878 A1 May 21, 2009

(30) Foreign Application Priority Data

Nov. 19, 2007 (JP) ................................. 2007-299089

(51) Int. Cl.
*A61M 5/315* (2006.01)
*A61M 37/00* (2006.01)
*A61M 5/00* (2006.01)

(52) U.S. Cl. .......... 604/218; 604/220; 604/228; 604/89; 604/187

(58) Field of Classification Search ................... 600/578; 604/89, 218, 228, 181, 187
See application file for complete search history.

(56) References Cited

U.S. PATENT DOCUMENTS

| 3,306,291 | A |   | 2/1967 | Burke |         |
|-----------|---|---|--------|-------|---------|
| 3,881,484 | A | * | 5/1975 | Gidcumb, Jr. | 604/89 |
| 4,213,456 | A | * | 7/1980 | Bottger | 604/226 |
| 4,613,326 | A | * | 9/1986 | Szwarc | 604/89 |
| 4,690,154 | A | * | 9/1987 | Woodford et al. | 600/578 |
| 5,788,677 | A | * | 8/1998 | Botich et al. | 604/195 |

FOREIGN PATENT DOCUMENTS

| JP | 6-327771 A   | 11/1994 |
| JP | 2006327771   | 12/2006 |
| WO | WO0105456    | 1/2001  |
| WO | W02006/007592 | 1/2006 |

OTHER PUBLICATIONS

Search Report for European Patent App. No. 08019559.7 ( Mar. 5, 2009).

* cited by examiner

*Primary Examiner* — Theodore Stigell
*Assistant Examiner* — Bradley Thomas, Jr.
(74) *Attorney, Agent, or Firm* — Kenealy Vaidya LLP (57) ABSTRACT

A plunger rod useful for sliding a piston inserted in a syringe barrel has a threaded portion formed at an end of the plunger rod to attach the piston on the plunger rod and a flange formed at an opposite end of the plunger rod. The threaded portion and the flange are integrally connected together by a cylindrical member having an outer diameter such that the cylindrical member can be inserted with contact slidability in the syringe barrel, for example, an outer diameter equal to or slightly smaller than an inner diameter of the syringe barrel.

18 Claims, 10 Drawing Sheets

PLUNGER ROD AND SYRINGE

CROSS-REFERENCE TO RELATED APPLICATION

This application claims the priority of Japanese Patent Application 2007-299089 filed Nov. 19, 2007, which is incorporated herein by reference.

FIELD OF THE INVENTION

This invention relates to a plunger rod useful for supporting and sliding a piston inserted in a syringe barrel, and also to a syringe.

BACKGROUND OF THE INVENTION

With syringes, it has been common practice to draw medicaments into syringe barrels upon use. In recent years, however, prefilled syringes with medicaments already filled in syringe barrels have been developed to reduce the work load in medical care practice. Further, prefilled syringes with medicaments such as contrast media filled in syringe barrels thereof are finding increasing utility recently. In addition, prefilled plastic syringe barrels with medicaments such as contrast media filled in plastic syringe barrels of relative large capacities are also in use in recent years.

When using such a syringe barrel, a piston is attached to a forward end of a plunger rod by inserting the plunger rod into the syringe barrel through a rear end thereof and bringing a threaded portion, which is formed on a forward end of the plunger rod, into threaded engagement with a rear face of the piston. By sliding the piston, which is attached to the forward end of the plunger rod as described above, via the plunger rod, drawing or dispensing of a medicament is performed.

When attaching the piston to the forward end of the plunger rod as described above, the threaded portion at the forward end of the plunger rod cannot be smoothly brought into threaded engagement with the rear face of the piston unless a central axis of the syringe barrel and that of the plunger rod are brought into alignment. If the piston is attached to the threaded portion on the forward end of the plunger rod with the central axis of the syringe barrel and that of the plunger rod being out of alignment, the piston on the forward end of the plunger rod comes into a misaligned attitude so that the piston is no longer allowed to smoothly slide in the syringe barrel.

Even when the piston and the plunger rod are properly attached together, the plunger rod may be pushed in a misaligned attitude if there is clearance between an outer wall of the plunger rod and an inner wall of the syringe barrel. As a consequence, the piston may be caused to slide with its axis offset from parallel to the central axis of the syringe barrel, leading to a potential problem that fluid leakage may take place at the clearance.

As a method for solving the above-described problem, it has been proposed to use a cross-sectionally cruciform plunger rod formed by turning one of two rectangular plates, which have long axes in a direction of a central axis of a syringe barrel, over 90 degrees relative to the other while maintaining their long axes aligned together (JP-A-06-327771). With a plunger rod of this construction, the direction of force applied to the plunger rod may become out of alignment with the sliding direction of the piston, and therefore, fluid leakage may take place when drawing or dispensing a medicament or the like which requires high sealing performance. Described specifically, when the plates maintained in contact with the inner wall of the syringe barrel are cruciform in cross-section, the setting of the plates at a width substantially equal to the inner diameter of the syringe barrel makes it possible to prevent the plunger rod from becoming out of alignment when force is applied in the plane direction of any one of the plates, because the corresponding plate is in contact with the inner wall of the syringe barrel. Against force in a direction other than the plane directions of the plates, however, the plates cannot function, leading to a potential problem that the piston may be misaligned to cause fluid leakage or the like.

As a method for overcoming the above-mentioned potential problem, it has been proposed to use a plunger rod with a disk-shaped partition, which has a diameter equal to the widths of the plates, arranged at right angles relative to the central axis of the plunger rod around the above-described cross-sectionally cruciform plunger rod (WO 2001/005456). Even with this overcoming method, it is still impossible to prevent misalignment of the plunger rod at portions where the partition is not arranged, so that fluid leakage cannot be prevented completely.

SUMMARY OF THE INVENTION

An object of the present invention is, therefore, to provide a plunger rod for a syringe, said plunger rod permitting easy attachment of a piston to a threaded portion at a forward end of the plunger rod with a central axis of a syringe barrel and that of the plunger rod being readily maintained in alignment with each other; and also making it possible to prevent the piston from being caused to slide in an attitude that the central axis of the piston is offset from parallel to the central axis of the syringe barrel. Another object of the present invention is to provide a syringe provided with such a plunger rod.

The above-described objects can be achieved by the present invention to be described hereinafter. Described specifically, in one aspect of the present invention, there is thus provided a plunger rod useful for supporting and sliding a piston inserted in a syringe barrel, said plunger rod having a threaded portion formed at an end of the plunger rod to attach the piston on the plunger rod and a flange formed at an opposite end of the plunger rod, wherein the threaded portion and the flange are integrally connected together by a cylindrical member having an outer diameter such that the cylindrical member can be inserted with contact slidability in the syringe barrel.

In the above-described present invention, the plunger rod may further comprise a thumb support member arranged in a hollow opening formed in the flange on the cylindrical member; and the thumb support member may preferably comprise plural ribs arranged along a direction of a length of the cylindrical member at least inside the cylindrical member. For example, the plural ribs may be formed in a cross-sectionally cruciform shape, or may be partially cut off along a central axis of the cylindrical member. Preferably, the thumb support member may also comprise a plug fitted in the hollow opening formed in the flange on the cylindrical member. Preferably, the threaded portion may be a short cylinder, and plural ribs may be formed inside the short cylinder. Preferably, the plunger rod may be integrally formed in an entirety thereof with at least one resin selected from the group consisting of cyclic olefin resins, radiation-resistant polypropylene resin and polypropylene resin.

In another aspect of the present invention, there is also provided a syringe comprising a syringe barrel set having a syringe barrel, which is provided at an end thereof with a medicament delivery tip sealed with a closure and is open at an opposite end thereof, and a piston having a screw bore formed along a central axis of the piston in a rear portion of the piston and slidably sealing the open end of the syringe barrel; and the above-described plunger rod according to the present invention.

According to the present invention, it is possible to provide a plunger rod for a syringe. The plunger rod permits easy attachment of a piston to a threaded portion at a forward end of the plunger rod with a central axis of a syringe barrel and that of the plunger rod being readily maintained in alignment with each other, and further, can prevent the piston from being caused to slide in an attitude that the central axis of the piston is offset from parallel to the central axis of the syringe barrel. In addition, the plunger rod does not cause fluid leakage. The present invention can provide a syringe, which is provided with such a plunger rod and has similar advantages as the above-described plunger rod.

DETAILED DESCRIPTION OF THE INVENTION AND PREFERRED EMBODIMENTS

The present invention will hereinafter be described in further detail with reference to the accompanying drawings illustrating best modes for practicing the present invention. As illustrated in FIGS. 1, 2A, 2B and 3, a plunger rod 50 according to the first embodiment of the present invention is useful for supporting and sliding a piston 12 inserted in a syringe barrel 11. On an end of the plunger rod 50, a threaded portion 1 is formed to permit attachment of the piston 12, and on an opposite end of the plunger rod 50, a flange 2 is formed. The threaded portion 1 and the flange portion 2 are integrally connected together by a cylindrical member 3 having an outer diameter such that the cylindrical member 3 can be inserted with contact slidability in the syringe barrel, specifically an outer diameter either equal to or slightly smaller than an inner diameter of the syringe barrel 11.

Figure 1:
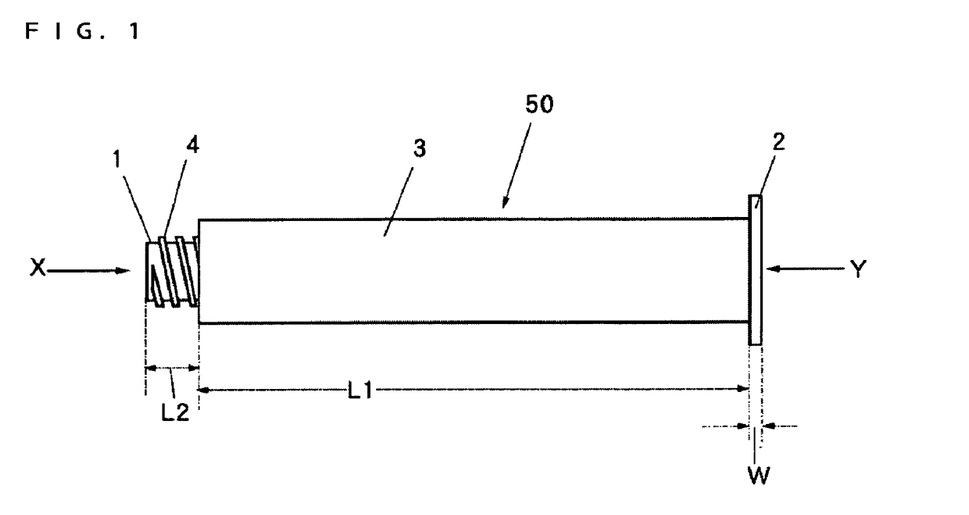
FIG. 1 is a side view of a plunger rod according to a first embodiment of the present invention.
Figure 2A:
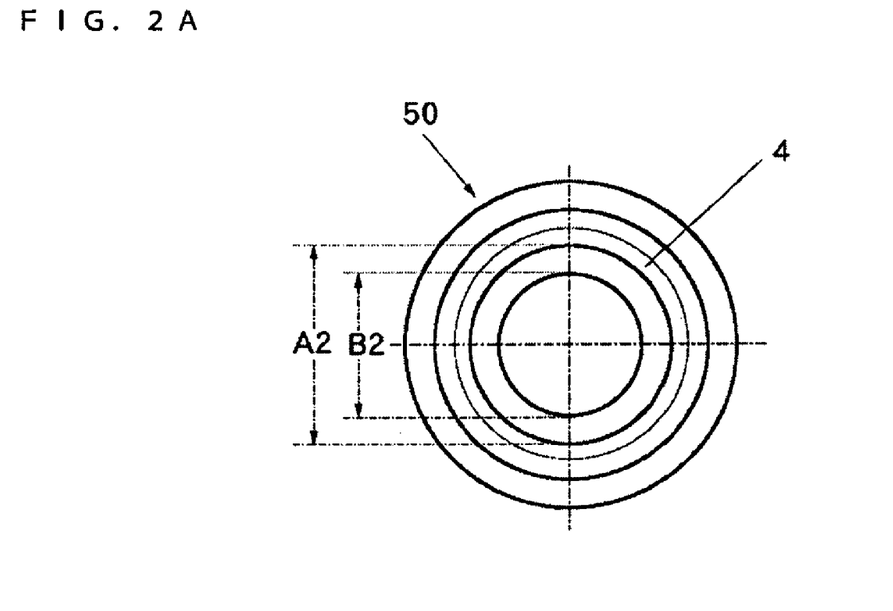
FIG. 2A is an enlarged front view in the direction of arrow X in FIG. 1.
Figure 2B:
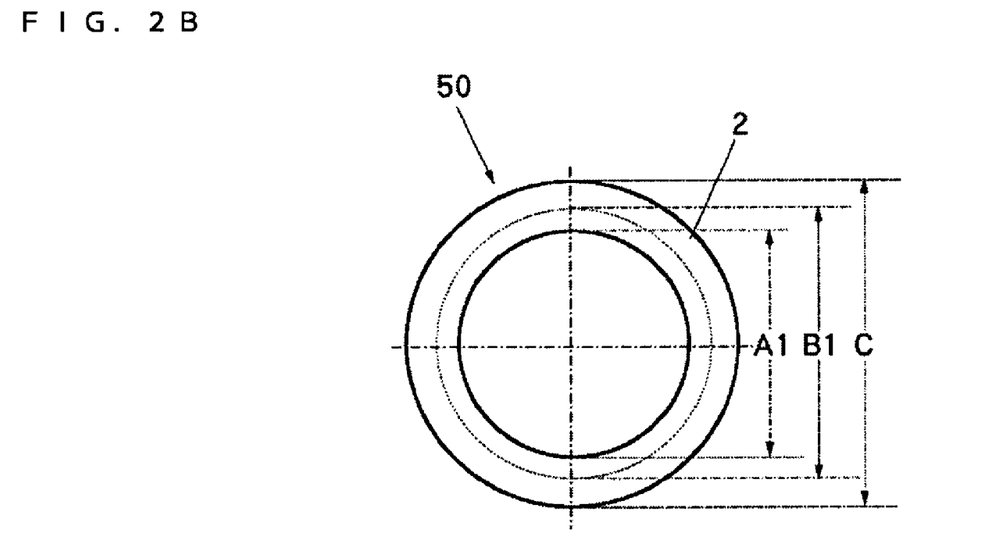
FIG. 2B is an enlarged rear view in the direction of arrow Y in FIG. 1.

The plunger rod 50 can be integrally molded by injection molding with at least one resin selected from the group consisting of cyclic olefin resins, radiation-resistant polypropylenes, polypropylene, polycarbonates and polystyrene. The cylindrical member 3 can have the following dimensions— inner diameter (A1): approx. 1 to 48 mm, outer diameter (B1) approx. 3 to 50 mm (wall thickness: approx. 1 to 3 mm), and length (L1): approx. 30 to 200 mm. The main body of the threaded portion 1 arranged on one of the ends of the cylindrical member 3 is cylindrical, and can have the following dimensions—outer diameter (A2): approx. 2 to 40 mm, inner diameter (B2): approx. 4 to 38 mm (wall thickness: approx. 0.5 to 3 mm), and length (L2): approx. 3 to 20 mm. Threads 4 are arranged on the surface of the main body of the threaded portion 1. On the other hand, the flange 2 formed on the opposite end of the cylindrical member 3 has the following dimensions—outer diameter (C): approx. 10 to 50 mm, and thickness (W): approx. 1 to 5 mm.

Figure 3:
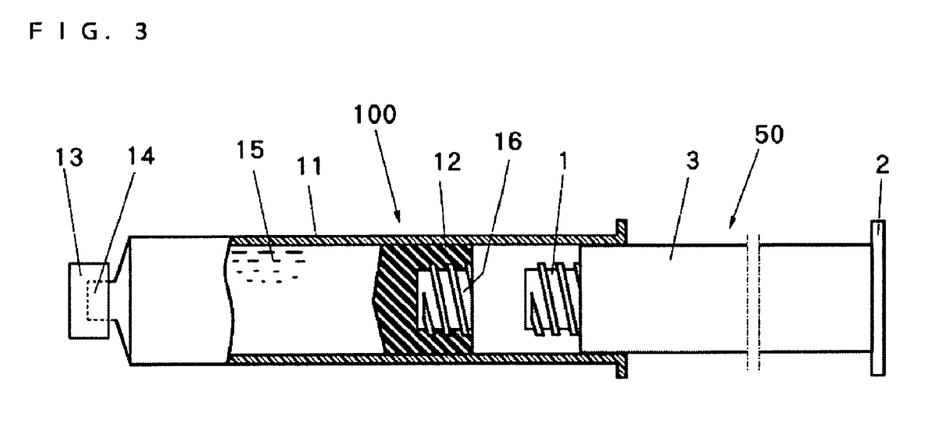
FIG. 3 is a partly cross-sectional view of a syringe according to the present invention, which is equipped with the plunger rod of FIG. 1.

The state of the plunger rod 50 according to the first embodiment of the present invention in its use is illustrated in FIG. 3. When it is desired to use the plunger rod 50 according to the first embodiment of the present invention with a medicament-prefilled syringe barrel 100, the plunger rod 50 is inserted through the rear end of the syringe barrel 11. When the plunger rod 50 is inserted through the rear end of the syringe barrel 11, the plunger rod 50 is accurately guided into the syringe barrel 11 because no clearance is formed between the outer wall of the cylindrical member 3 and the inner wall of the syringe barrel 11. As the syringe barrel 11 and the cylindrical member 3 are coaxial cylinders, respectively, the central axis of the syringe barrel 11 and the central axis of the plunger rod 50 are naturally brought into alignment.

The plunger rod 50 according to the first embodiment of the present invention, therefore, makes it possible to readily bring the central axis of the syringe barrel 11 and the central axis of the plunger rod 50 into alignment with each other without needing precise positioning or the like, so that the piston 12 can be attached to the end of the plunger rod 50 in a correct attitude (an attitude that the central axis of the piston 12 is in alignment with the central axis of the plunger rod 50. Owing to the existence of no clearance between the outer wall of the plunge rod 50 and the inner wall of the syringe barrel 11, the plunger rod 50 is not pushed in any misaligned attitude. The piston 12 is, therefore, allowed to smoothly slide in the syringe barrel 11, so that the sealing performance for the medicament 15 is not deteriorated and no fluid leakage takes place between the inner wall of the syringe barrel 11 and the outer wall of the piston 12.

With reference to FIGS. 4A, 4B, 5A, 5B and 6, a plunger rod 60 according to the second embodiment of the present invention will next be described. At least inside a cylindrical member 3, plural ribs 5A are formed as a thumb support member along the direction of the length of the cylindrical member 3. Described specifically, when the plunge rod 50 according to the first embodiment of the present invention is relatively large, for example, when the inner diameter (A1) of the cylindrical member 3 is 8 mm or greater, a part of the ball of the thumb may go into a rear end portion of the cylindrical member 3 upon use, and the comfort of its use may not be good in some instances. The formation of a thumb support member by the plural ribs 5A, however, can eliminate the above-described problem in the comfort of use. In the above-described second embodiment, two ribs 5A are formed, one in a vertical direction and the other in a horizontal direction, namely, in a cruciform shape. One or more ribs can, however, be employed insofar as the above-described advantageous effect (the provision of a support for the thumb) can be brought about. It is to be noted that the ribs 5A are formed over the entire length of the cylindrical member 3 for the convenience of the integral molding of the plunger rod 60.

Figure 4A:
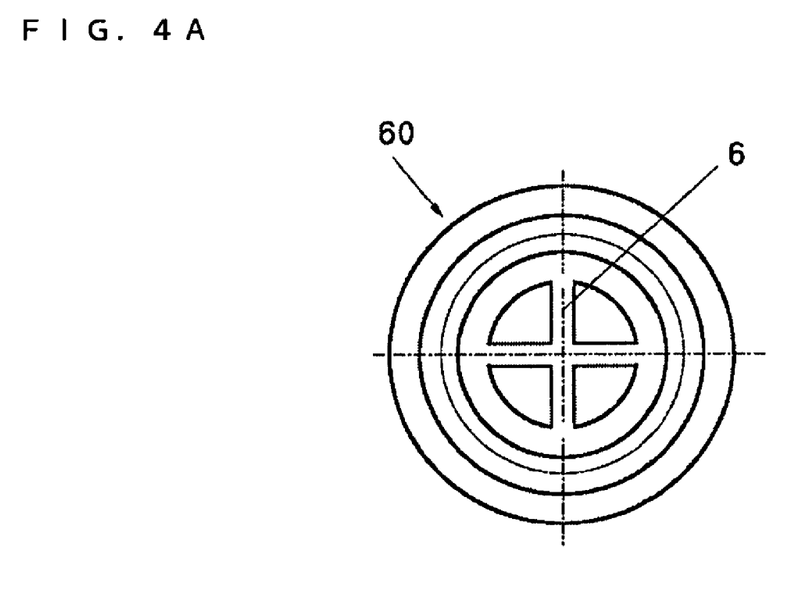
FIGS. 4A and 4B are similar to FIGS. 2A and 2B, but show a plunger rod according to a second embodiment of the present invention.
Figure 4B:
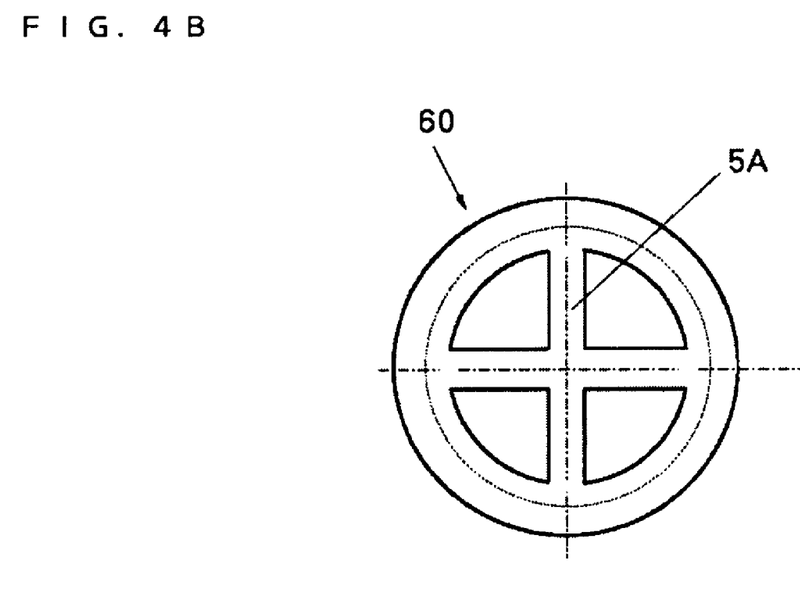
Figure 5A:
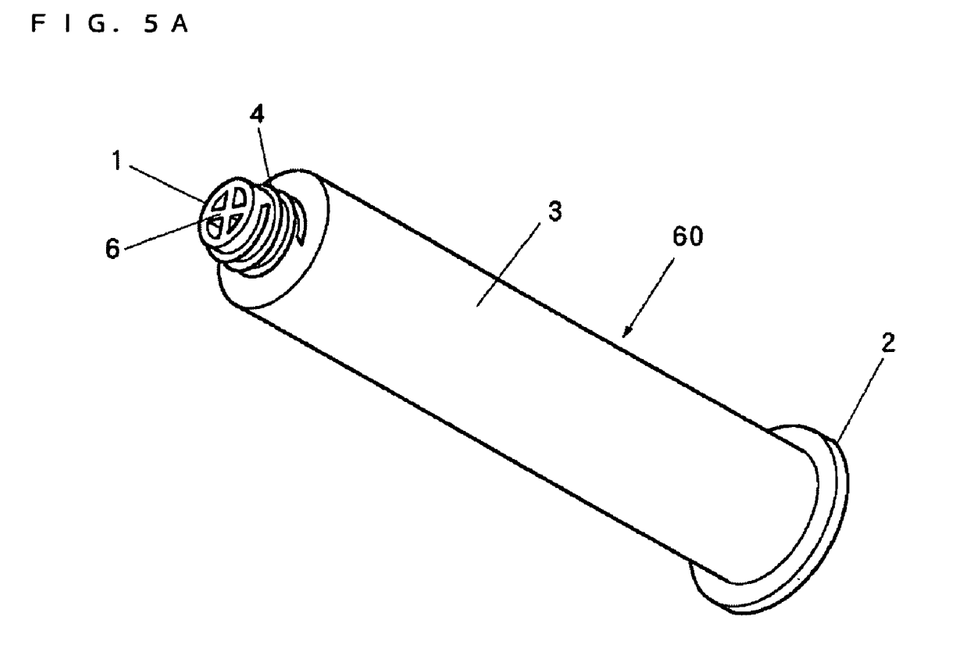
FIGS. 5A and 5B area downward and upward, perspective views of the plunger rod according to the second embodiment of the present invention.
Figure 5B:
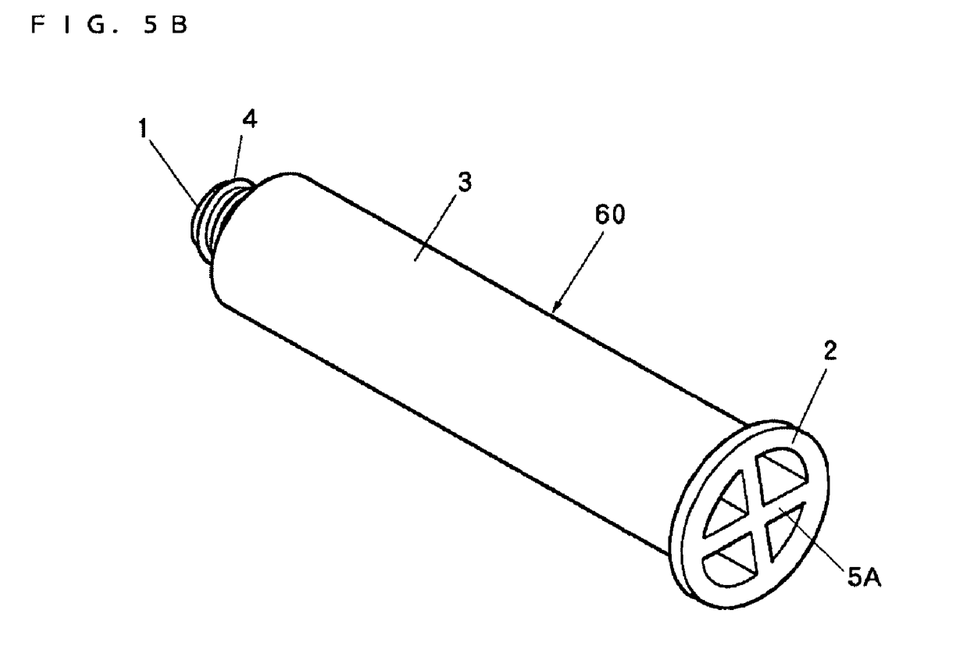
Figure 6:
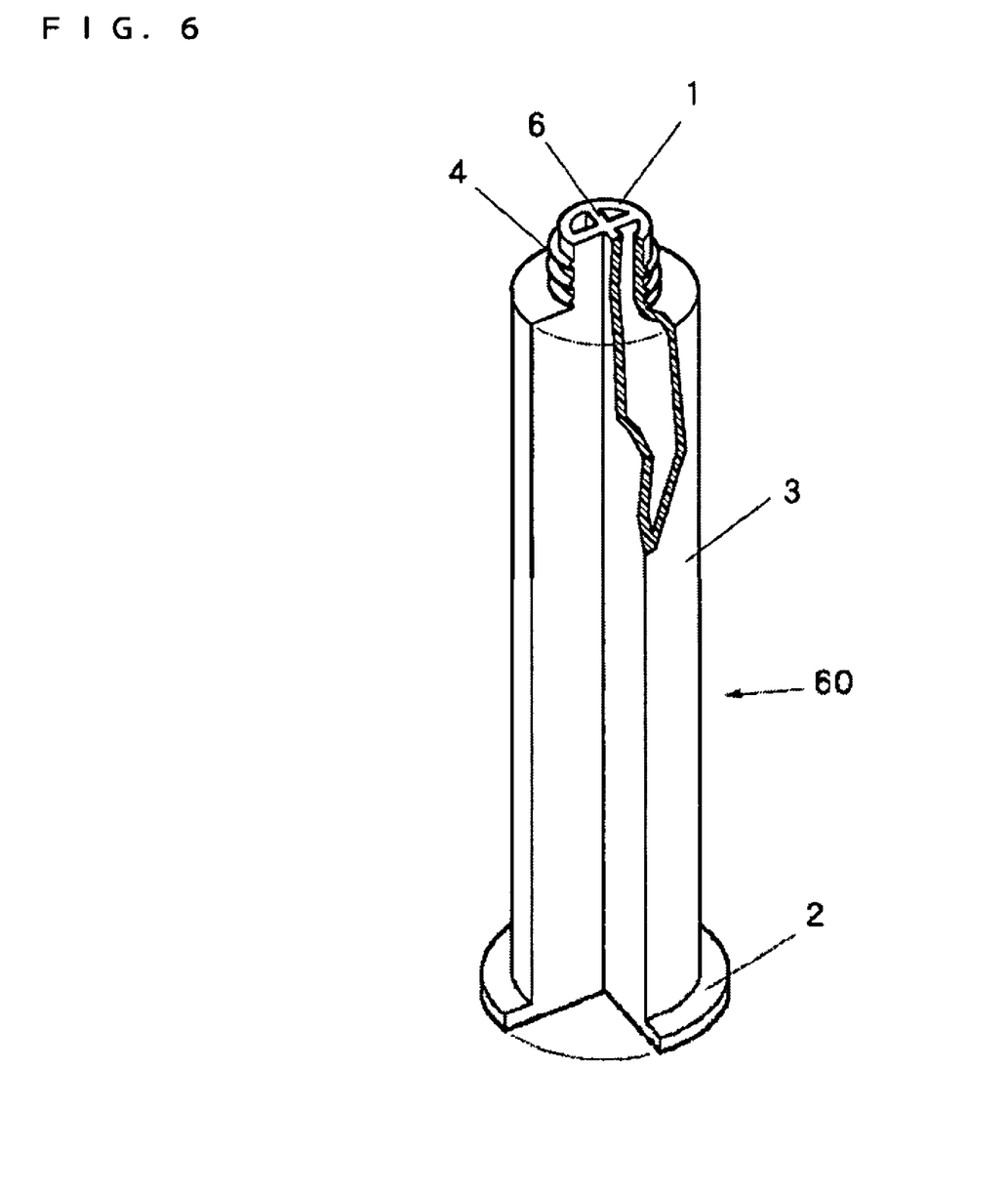
FIG. 6 is a partly cut-off, partly cross-sectional, perspective view of the plunger rod according to the second embodiment of the present invention.
Figure 7A:
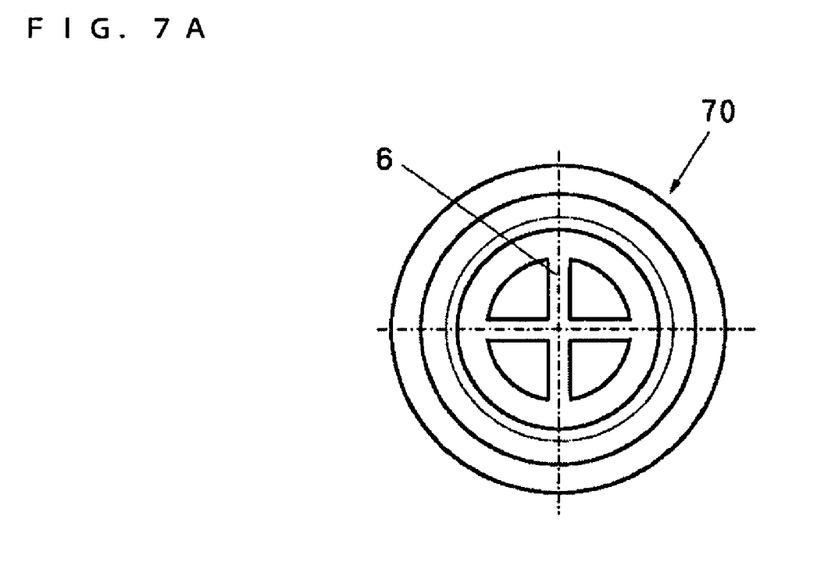
FIGS. 7A and 7B are similar to FIGS. 2A and 2B, but show a plunger rod according to a third embodiment of the present invention.
Figure 7B:
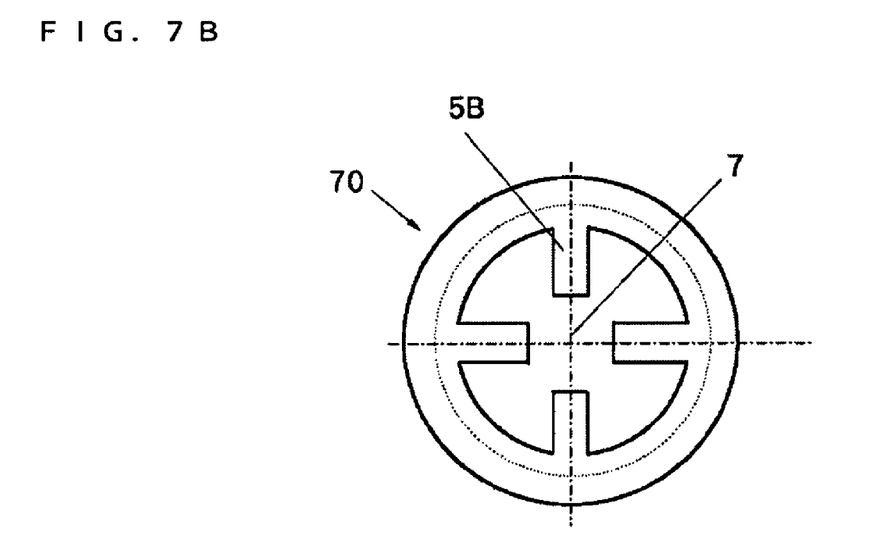
Figure 8A:
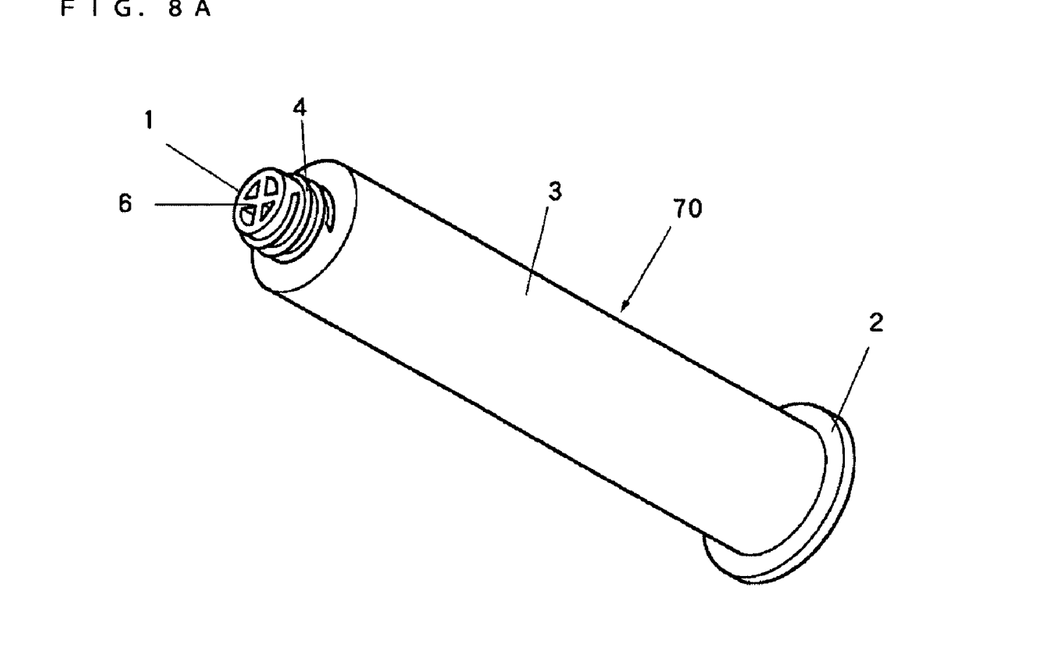
FIGS. 8A and 8B are a downward and upward, perspective views of the plunger rod according to the third embodiment of the present invention.
Figure 8B:
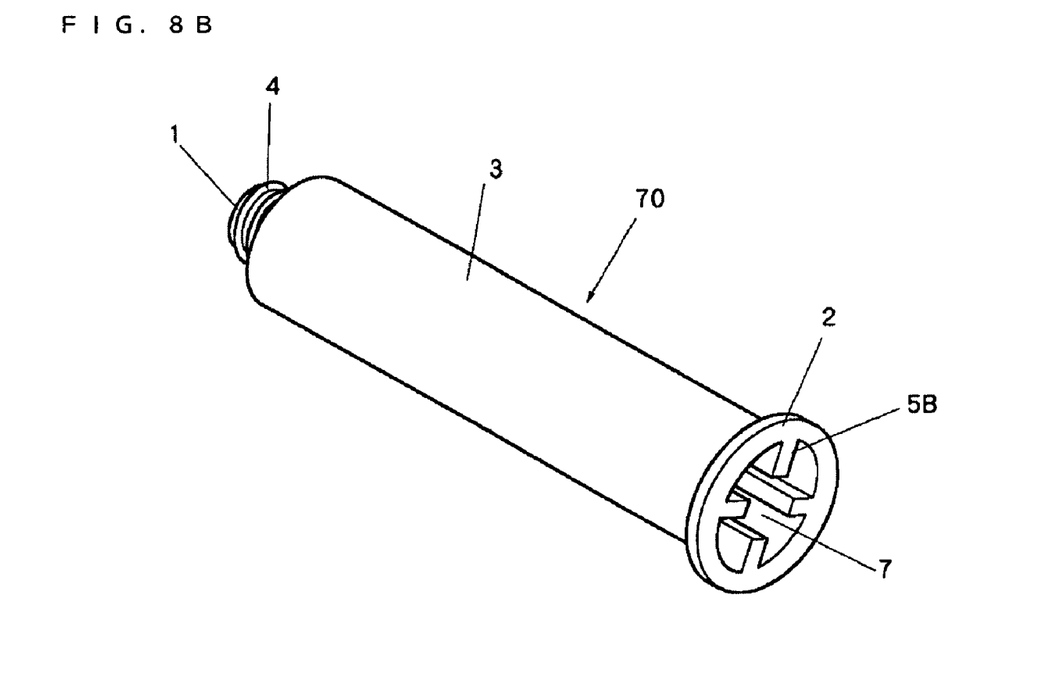
Figure 9:
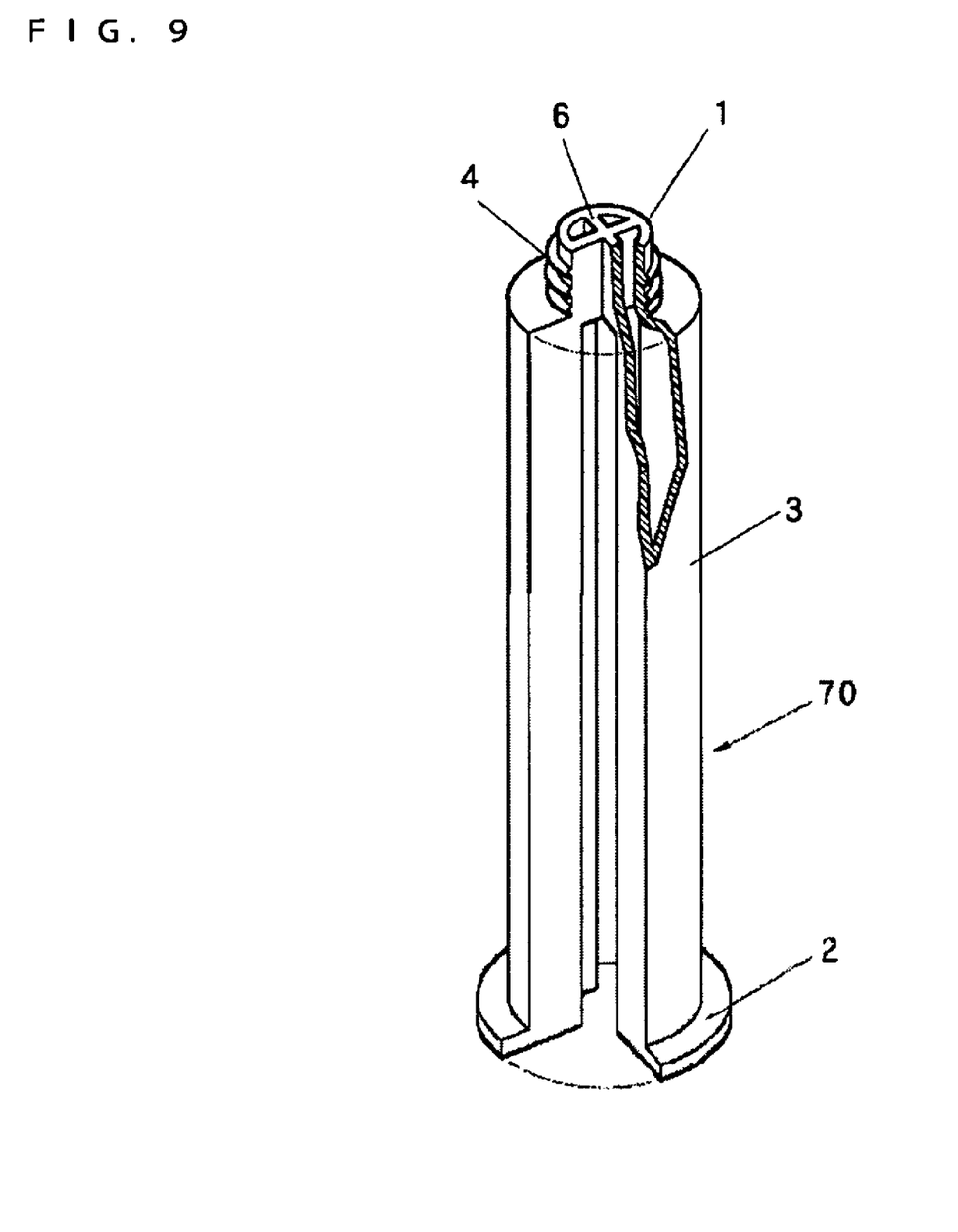
FIG. 9 is a partly cut-off, partly cross-sectional, perspective view of the plunger rod according to the third embodiment of the present invention.

As depicted in FIG. 4A, the main body of the threaded portion 1 is arranged in the form of a short cylinder for the convenience of its injection molding, and similar to the ribs 5A, ribs 6 are also arranged in the short cylinder. The formation of the ribs 6 is not essential, but by the formation of the ribs 6, the piston 12 can be protected from deformations during the sliding movement of the piston 12. It is, therefore, preferred to arrange the rib 6. The ribs 6 are not limited to the illustrated cruciform arrangement, and can be arranged in any form and dimensions insofar as they are shaped and dimensioned to come into contact with an end of a screw bore 16 formed in a rear portion of the piston 12. However, a cruciform arrangement is particularly preferred from the standpoints of the readiness and economy of molding.

FIGS. 7A, 7B, 8A, 8B and 9 depict a plunger rod 70 according to the third embodiment of the present invention. In this third embodiment, the plural ribs 5A (as the thumb support member) are partly cut off to form cut-off portions 7. Described specifically, ribs are now assumed to be arranged integrally with a cylindrical member as in the second embodiment. When such a molding is removed from the mold and cooled subsequent to its injection molding, the resin undergoes cooling shrinkage so that the cross-sectional roundness of the cylindrical member is reduced to some extent. The reduction in the cross-sectional roundness due to the above-described cooling shrinkage is not much, and is still within a practically acceptable range. By including the above-described cut-off portions 7, however, the above-described reduction in the cross-sectional roundness due to cooling shrinkage can be eliminated to provide improved contact slidability between the outer wall of the cylindrical member 3 and the inner wall of the syringe barrel 11, so that fluid leakage can be avoided more completely.

Figure 10:
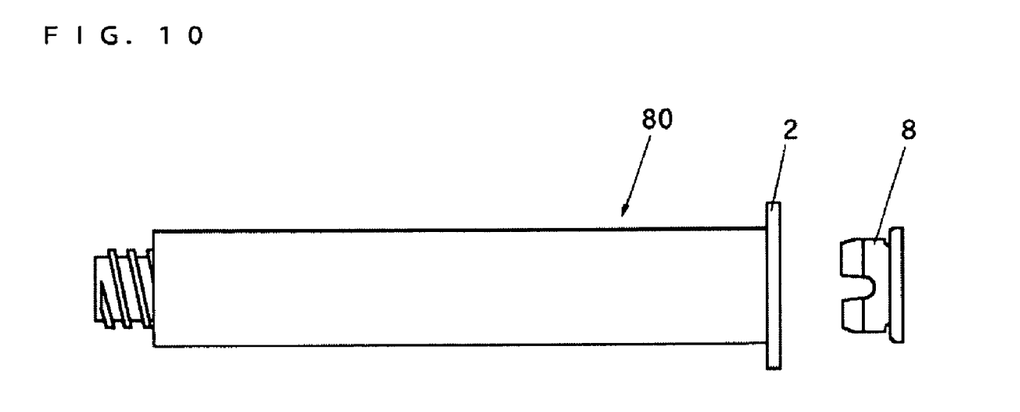
FIG. 10 is a side view of a plunger rod according to a fourth embodiment of the present invention.

In the above-described second and third embodiments, the plural ribs 5A, 5B are used as thumb support members, respectively. It is to be noted that the thumb support member is not limited to the ribs 5A or 5B and that any means can be adopted insofar as the thumb can be prevented from going into a rear end portion of a plunger rod. As illustrated in FIG. 10, the thumb support member can be, for example, a plug 8 closing a hollow opening formed in a flange 2 of a plunger rod 80 according to the fourth embodiment of the present invention. This plug 8 is not limited to the illustrated example, and can take any other form, for example, can be a cap insofar as it can support the thumb. Concerning the material of the plug 8, it may be formed of the same material as the plunger rod or may be formed of a rubber similar to that employed for rubber plugs.

As depicted in FIG. 3, the present invention also provides a syringe composed of a syringe barrel set and the above-described plunger rod according to the present invention. The syringe may be a prefilled syringe with a medicament filled therein. Using the plunger rod 50 according to the first embodiment as one example of the plunger rod according to the present invention, a description will hereinafter be made about a prefilled syringe according to the present invention. As shown in FIG. 3, the prefilled syringe is composed of a medicament-prefilled syringe barrel set 100 and the plunger rod 50 according to the present invention. The medicament-prefilled syringe barrel set 100 includes the syringe barrel 11, the piston 12 slidably inserted in the syringe barrel 11, and a medicament 15 dispensably sealed by the piston 12 within the syringe barrel 11. The syringe barrel 11 is equipped at an end thereof with a medicament delivery tip 14 sealed by a suitable closure 13, and is open at an opposite end thereof.

The medicament-prefilled syringe barrel set 100 may have a similar construction as conventional medicament-prefilled syringe barrel sets, except that the piston 12 is provided at the rear end portion thereof with the screw bore 16 with which the threaded portion 1 of the plunger rod 50 according to the present invention can be brought into threaded engagement and that the syringe barrel 11 has an inner diameter such that the cylindrical member 3 of the plunger rod 50 can be inserted with contact slidability in the syringe barrel 11, for example, an inner diameter either equal to or somewhat greater than the outer diameter of the cylindrical member 3 of the plunger rod 50. For example, the syringe barrel 11 can be made of glass or a resin such as a cyclic polyolefin. The medicament delivery tip 14 arranged at one end of the syringe barrel 11 is sealed with the suitable closure 13, for example, a rubber cap of excellent chemical resistance or a rubber cap covered with a plastic film having excellent chemical resistance. The medicament 15 prefilled within the syringe barrel 11 can be, for example a desired medicament such as a contrast medium, and is sealed by the piston 12 which can be made, for example, of rubber of excellent chemical resistance or rubber covered with a plastic film having excellent chemical resistance.

With reference to FIG. 3, a description will now be made about the manner of use of the syringe according to the present invention. First, a forward end portion of the plunger rod 50 according to the present invention is inserted through the read end of the syringe barrel 11. When the forward end of the plunger rod 50 is inserted through the rear end of the syringe barrel 11 as mentioned above, the plunger rod 50 is guided by the inner wall of the syringe barrel 11 because no clearance is formed between the outer wall of the cylindrical member 3 of the plunger rod 50 and the inner wall of the syringe barrel 11. As a consequence, the central axis of the plunger rod 50 is naturally brought into alignment with the central axis of the syringe barrel 11. With the central axis of the plunger rod 50 maintained in alignment with the central axis of the syringe barrel 11 as described above, the plunger rod 50 is pushed straight into the syringe barrel 11, and further, the plunger rod 50 is turned to bring the threaded portion 1, which is arranged at the forward end of the plunger rod 50, into threaded engagement with the screw bore 16 formed along the central axis of the piston in the rear end portion of the piston 12. To the free end of the plunger rod 50, the piston 12 can be attached in a correct attitude (i.e., in the attitude that the central axis of the piston 12 is in alignment with the central axis of the plunger rod 50).

Also as depicted in FIG. 3, the rubber closure 13 by which the medicament delivery tip 14 of the syringe barrel 11 is sealed is then removed, and to the medicament delivery tip 14, a syringe needle or a free end of an extension tube is fitted, for example. By pushing the piston 12 via the plunger rod 50, the medicament 15 can be injected or otherwise delivered to an intended site, for example, into the body via the syringe needle, the extension tube or the like. As substantially no clearance is formed between the outer wall of the plunger rod 50 and the inner wall of the syringe barrel 11 during the pushing of the piston 12, the piston can be prevented from sliding in an attitude misaligned with the central axis with the syringe barrel 11. It is, therefore, possible to prevent the occurrence of fluid leakage.

The invention claimed is:

1. A plunger rod useful for supporting and sliding a piston inserted in a syringe barrel, said plunger rod having a threaded portion formed at an end of said plunger rod to attach said piston on said plunger rod and a flange formed at an opposite end of said plunger rod, wherein:
  said threaded portion and said flange are integrally connected together by a cylindrical member having an outer diameter such that said cylindrical member can be inserted with contact slidability in said syringe barrel, and
  said threaded portion is a short cylinder, and plural ribs are formed inside said short cylinder.

2. A plunger rod according to claim 1, further comprising a thumb support member arranged in a hollow opening formed in said flange on said cylindrical member.

3. A plunger rod according to claim 2, wherein said thumb support member comprises plural ribs arranged along a direction of a length of said cylindrical member at least inside said cylindrical member.

4. A plunger rod according to claim 3, wherein said plural ribs are formed in a cross-sectionally cruciform shape.

5. A plunger rod according to claim 3, wherein said plural ribs are partially cut off along a central axis of said cylindrical member.

6. A plunger rod according to claim 2, wherein said thumb support member comprises a plug fitted in said hollow opening formed in said flange on said cylindrical member.

7. A plunger rod according to claim 1, wherein said plunger rod is integrally formed in an entirety thereof with at least one resin selected from the group consisting of cyclic olefin resins, radiation-resistant polypropylenes, polypropylene, polycarbonates and polystyrene.

8. A syringe comprising:
  a syringe barrel set having a syringe barrel, which is provided at an end thereof with a medicament delivery tip sealed with a closure and is open at an opposite end thereof, and a piston having a screw bore formed along a central axis of said piston in a rear portion of said piston and slidably sealing said open end of said syringe barrel; and
  a plunger rod as defined in claim 1.

9. A plunger rod useful for supporting and sliding a piston inserted in a syringe barrel, said plunger rod having a threaded portion formed at an end of said plunger rod to attach said piston on said plunger rod and a flange formed at an opposite end of said plunger rod, wherein:
  said threaded portion and said flange are integrally connected together by a cylindrical member having an outer diameter such that said cylindrical member can be inserted with contact slidability in said syringe barrel; and
  a thumb support member is arranged in a hollow opening formed in said flange on said cylindrical member, wherein said thumb support member comprises plural ribs arranged along a direction of a length of said cylindrical member at least inside said cylindrical member, and said plural ribs are formed in a cross-sectionally cruciform shape.

10. A plunger rod according to claim 9, wherein said plural ribs are partially cut off along a central axis of said cylindrical member.

11. A plunger rod according to claim 9, wherein said thumb support member comprises a plug fitted in said hollow opening formed in said flange on said cylindrical member.

12. A plunger rod according to claim 9, wherein said plunger rod is integrally formed in an entirety thereof with at least one resin selected from the group consisting of cyclic olefin resins, radiation-resistant polypropylenes, polypropylene, polycarbonates and polystyrene.

13. A syringe comprising:
  a syringe barrel set having a syringe barrel, which is provided at an end thereof with a medicament delivery tip sealed with a closure and is open at an opposite end thereof, and a piston having a screw bore formed along a central axis of said piston in a rear portion of said piston and slidably sealing said open end of said syringe barrel; and
  a plunger rod as defined in claim 9.

14. A plunger rod useful for supporting and sliding a piston inserted in a syringe barrel, said plunger rod having a threaded portion formed at an end of said plunger rod to attach said piston on said plunger rod and a flange formed at an opposite end of said plunger rod, wherein:
  said threaded portion and said flange are integrally connected together by a cylindrical member having an outer diameter such that said cylindrical member can be inserted with contact slidability in said syringe barrel; and
  a thumb support member is arranged in a hollow opening formed in said flange on said cylindrical member, wherein said thumb support member comprises plural ribs arranged along a direction of a length of said cylindrical member at least inside said cylindrical member, and said plural ribs are partially cut off along a central axis of said cylindrical member.

15. A plunger rod according to claim 14, wherein said plural ribs are formed in a cross-sectionally cruciform shape.

16. A plunger rod according to claim 14, wherein said thumb support member comprises a plug fitted in said hollow opening formed in said flange on said cylindrical member.

17. A plunger rod according to claim 14, wherein said plunger rod is integrally formed in an entirety thereof with at least one resin selected from the group consisting of cyclic olefin resins, radiation-resistant polypropylenes, polypropylene, polycarbonates and polystyrene.

18. A syringe comprising:
  a syringe barrel set having a syringe barrel, which is provided at an end thereof with a medicament delivery tip sealed with a closure and is open at an opposite end thereof, and a piston having a screw bore formed along a central axis of said piston in a rear portion of said piston and slidably sealing said open end of said syringe barrel; and
  a plunger rod as defined in claim 14.

* * * * *